United States Patent
Rokegem et al.

[11] Patent Number: 5,630,817
[45] Date of Patent: May 20, 1997

[54] ROD ATTACHMENT DEVICE FOR RACHIDIAN ORTHOPAEDY

[75] Inventors: Pascal Rokegem, Saint Laurent Blangy; Jean-Paul F. Steib, Strasbourg, both of France

[73] Assignee: Eurosurgical, Beaurains, France

[21] Appl. No.: 436,386

[22] PCT Filed: Nov. 17, 1993

[86] PCT No.: PCT/FR93/01128

§ 371 Date: Jul. 24, 1995

§ 102(e) Date: Jul. 24, 1995

[87] PCT Pub. No.: WO94/10929

PCT Pub. Date: May 26, 1994

[30] Foreign Application Priority Data

Nov. 18, 1992 [FR] France ............... 92 13868

[51] Int. Cl.⁶ ........................ A61B 17/56
[52] U.S. Cl. ............... 606/61; 606/60; 606/72; 606/73
[58] Field of Search ............... 606/60, 61, 69, 606/70, 71, 72, 73

[56] References Cited

U.S. PATENT DOCUMENTS

| | | | |
|---|---|---|---|
| 5,067,955 | 11/1991 | Cotrel | 606/61 |
| 5,176,680 | 1/1993 | Vignaud et al. | 606/73 |
| 5,368,594 | 11/1994 | Martin et al. | 606/61 |
| 5,380,326 | 1/1995 | Lin | 606/61 |
| 5,474,555 | 12/1995 | Puno et al. | 606/73 |
| 5,476,462 | 12/1995 | Allard et al. | 606/60 |

FOREIGN PATENT DOCUMENTS

| | | |
|---|---|---|
| 0392927 | 10/1990 | European Pat. Off. . |
| 0443894 | 8/1991 | European Pat. Off. . |
| 2638632 | 5/1990 | France . |
| 3924050 | 1/1991 | Germany . |
| WO94/26191 | 11/1994 | WIPO ............ 606/61 |

Primary Examiner—Michael Buiz
Assistant Examiner—Mark S. Leonardo
Attorney, Agent, or Firm—Steinberg, Raskin & Davidson, P.C.

[57] ABSTRACT

A device for the attachment to a rod (1) of a member (24) such as a screw, a hook or the like, in particular for spinal instrumentation. The device interacts with a smooth rod (1) and comprises an intermediate socket in the shape of a split ring (22) engageable on said rod. A tightening means (23) is arranged on the ring (22) at the split therein so that when it is tightened, the rod (1) protrudes from the ring while engaging the bottom of a U-shaped body to which the member is secured, whereas the free ends of the ring flanges (221, 222) engage both the rod (1) and the body (21). The device is useful in the field of orthopaedic equipment fitted during spinal surgery.

15 Claims, 5 Drawing Sheets

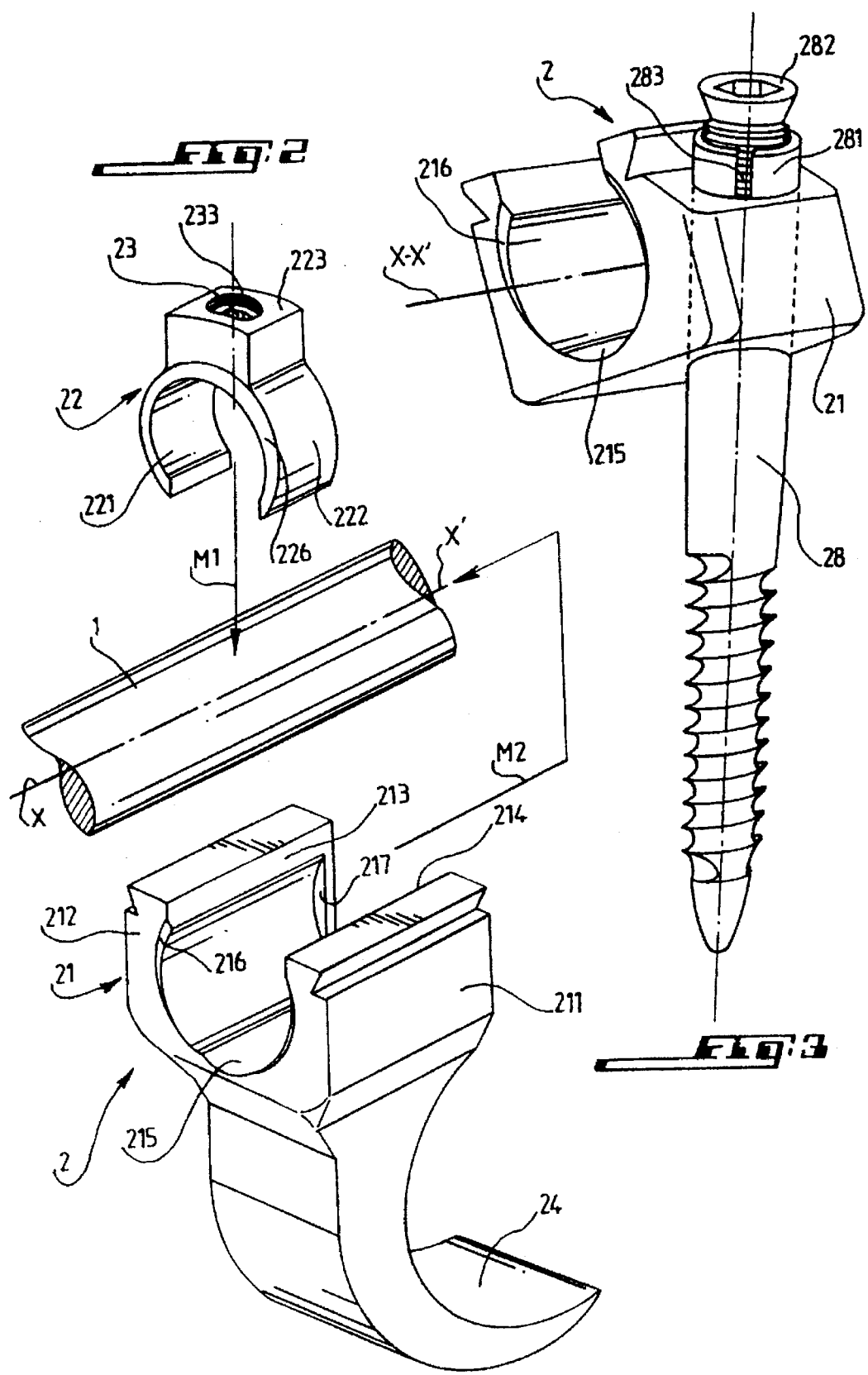

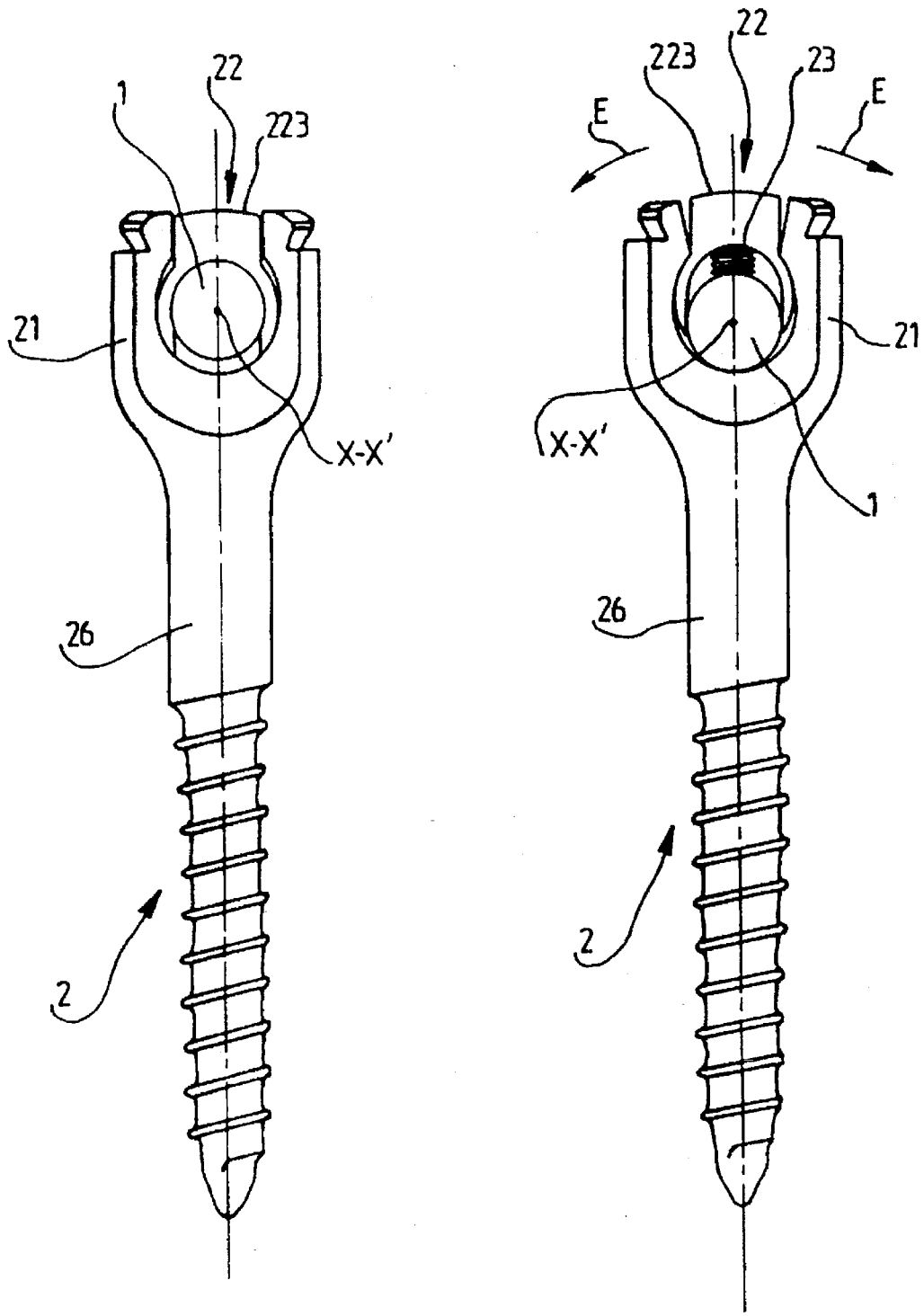

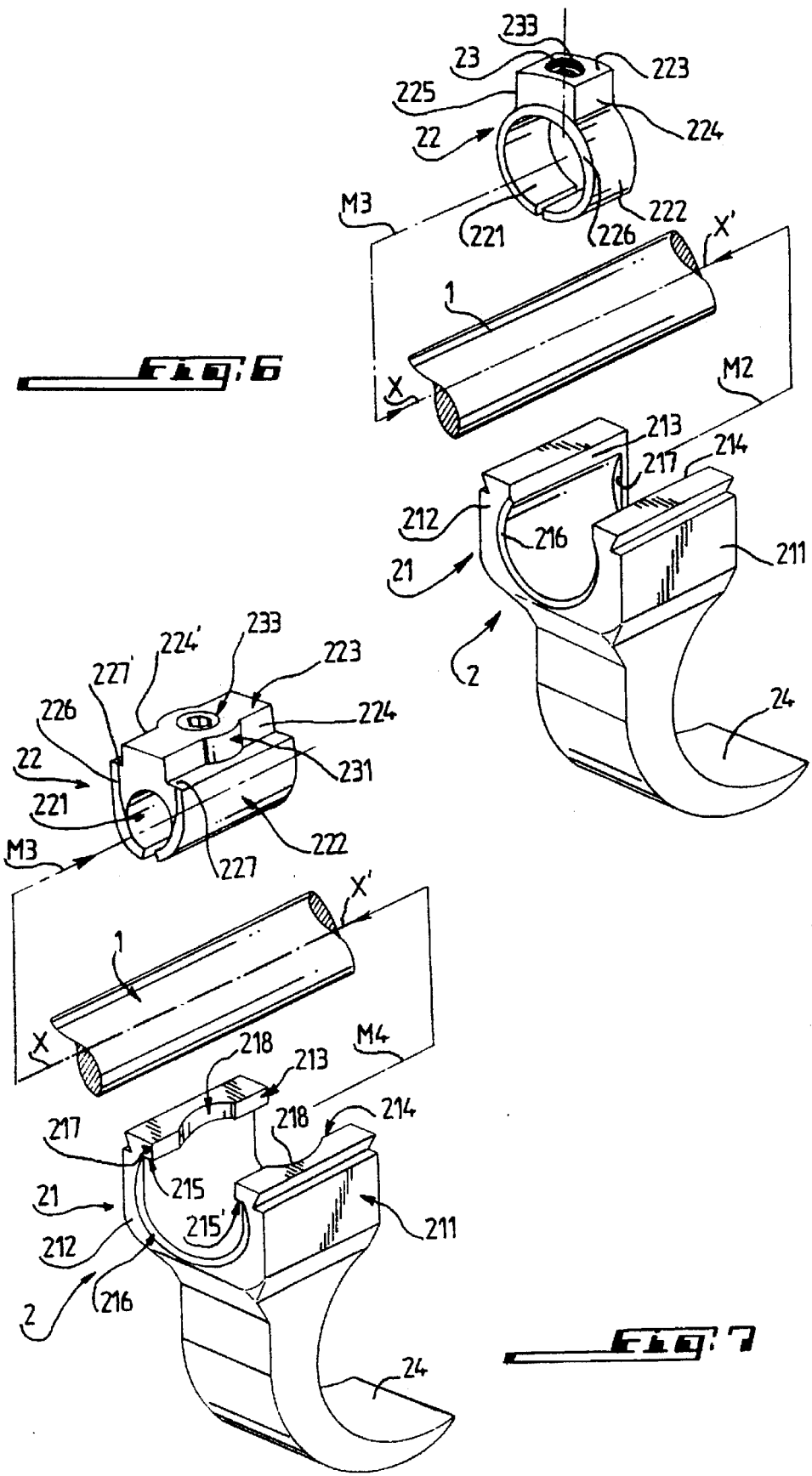

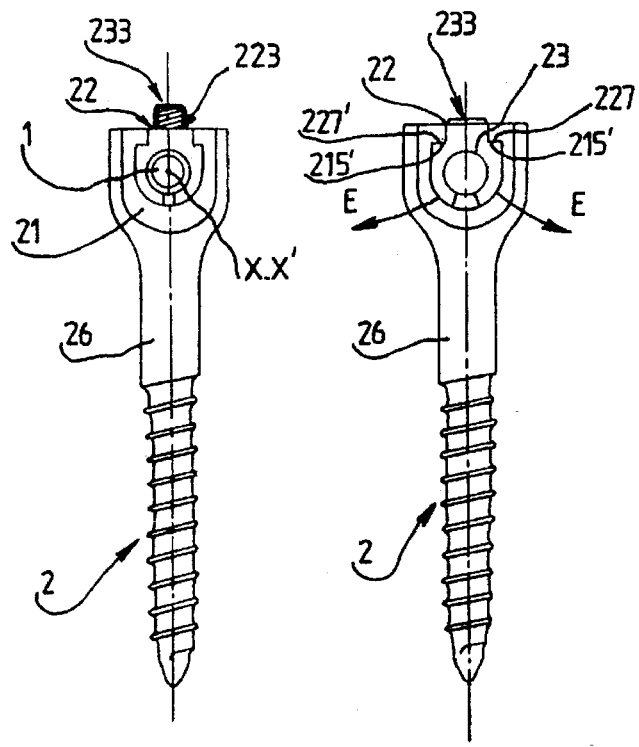
_Fig. 8_   _Fig. 9_
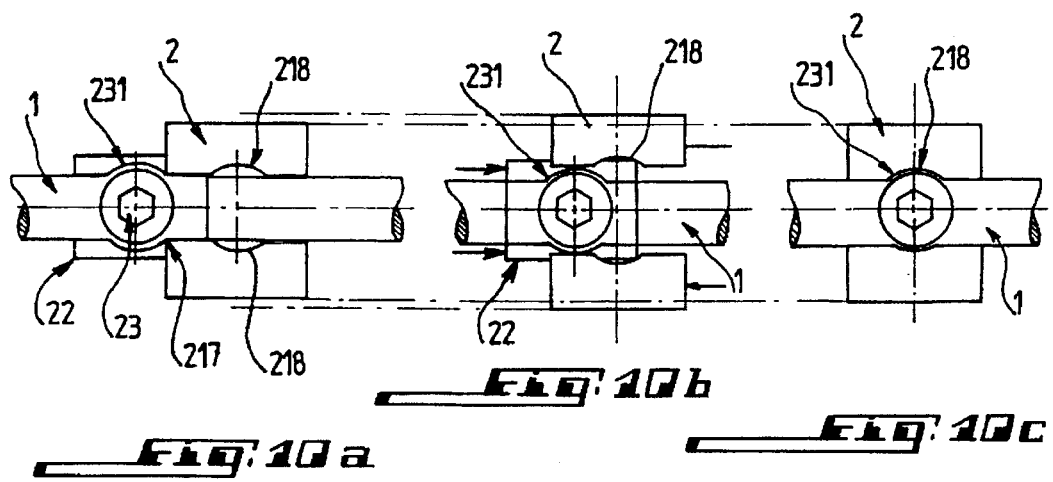
_Fig. 10a_   _Fig. 10b_   _Fig. 10c_

ROD ATTACHMENT DEVICE FOR RACHIDIAN ORTHOPAEDY

The present invention relates to a device for the fastening onto a rod of a member such as a screw, hook or the like in particular for a rachidian orthopaedy instrumentation.

One already knows various fit orthopaedic instrumentations or equipment such as those known under the name of HARRINGTON and which permit to straighten out and to stay the rachis or spinal column of a patient for example suffering from a scoliosis.

In these known orthopaedic instrumentations, members in particular provided to be anchored onto the vertebrae of the rachis to be propped, as for example like screws or hooks are connected to each other by a rod to which they are fastened. In general the fit orthopaedic contrivance comprises two rods the shape of which is defined in accordance with the position in which the rachis to be stayed should be held and which are implanted on either side, respectively, of the back face of this rachis.

Each member is held against motion on the corresponding rod with the assistance of a suitable fastening device. For example the document FR-A-2,458,271 (KEENE) describes an orthopaedic instrumentation in which each anchoring member is held immovable on a threaded rod through the medium of a fastening device comprising a U-shaped body made fast to the said member and between the legs of which the rod may be mounted radially. An intermediate sleeve may be mounted on the one hand onto the rod and on the other hand in sliding relationship between the legs of the body whereas clamping means are provided to exert a pressure upon the body through the medium of the sleeve.

One has also proposed in the prior art devices for the fastening of a member onto a rod comprising surface asperities such as knurls or chequerings. In these devices the clamping means are constituted by a set screw mounted onto the sleeve and adapted to exert a radial force upon the rod in order to make the latter fast to the sleeve by crushing the asperities to increase the adherence between the latter and the rod.

With these known devices however, the mounting of the sleeves onto the corresponding rod constitutes a complicated handling prior to putting the equipment in place thereby making wearisome and undesirably increasing the duration of the surgical operation necessary for the implanting of this appliance.

Moreover if the rod comprises machinings such as threadings or notches as this is the case with the KEENE or HARRINGTON instrumentations, the forces applied upon the members are generating concentrations of stresses at the level of the machinings of the rod which may cause its break.

Furthermore if the rod comprises surface asperities, the latter have a tendency to become battered at the level of its zones of contact with the sleeve or the screw so that the tightening hence the immobilization of the member onto the rod are frequently being altered after the implanting of the contrivance. In one case or in the other one, these defects may be detrimental to the behaviour of the anchoring members and be the cause of a modification of the geometry of the instrumentation. This geometry modification causes a loss of correction or of reduction and a mobilization of the anchoring members under the effect of the stresses imposed upon the patient.

The secondary effect of this mobilization may be the cause of a corrosion through friction called "fretting corrosion".

Therefore the present invention has as its object to propose a fastening device which copes in particular with the inconveniences of the prior art stated above.

To reach this goal the fastening device according to the invention is characterized in that the sleeve exhibits substantially the shape of a split ring which may be slipped over the advantageously smooth rod, the said clamping means being disposed onto the ring plumb with the slot thereof and in that the rod under the effect of the tightening exerted by the clamping means spreads apart the free ends of the wings of the slit ring in order that the free ends of the wings be radially pressed on the one hand upon the legs of the body which thus retain the ring within this body by a wedging effect and on the other hand upon the rod in order to hold it through clamping against motion.

According to an advantageous characteristic of the invention in a first embodiment, the sleeve exhibits the shape of a slit ring which may be radially engaged through elastic clamping or "clipping" with the rod and under the effect of the clamping exerted by the tightening means, the rod projects from the ring while being applied upon the bottom of the "U" of the body by producing the pressing effects and the aforesaid immobilization.

According to another advantageous characteristic of the invention and according to a second embodiment of the latter the sleeve exhibits the shape of a slit cylindrical ring which may be engaged with the advantageously smooth rod by being axially slipped thereon, the slot exhibiting a relatively small width so that in the spread apart state under the effect of the tightening means the rod keeps bearing upon those internal faces of the ends of the ring which define the slot.

According to still another advantageous characteristic of the invention, the ring comprises as being diametrally opposite to the slot, an outer radial advantageously prismatic protrusion comprising at least one face parallel to the axis of the ring and the U-shaped body comprises at the end of one of its legs a flat face parallel to the face of the ring and intended to come in contact with the latter when the ring is mounted in the said body and one of the two flat faces comprises a ramp-shaped portion and the other one a recess with a shape complementary of that of the ramp so that the ring be locked in the body through engagement of the ramp with the recess after the leg has been elastically moved away under the effect of the ramp co-operating with the confronting face during the assembly of the ring and of the body.

According to another advantageous characteristic of the invention, the prismatic protrusion comprises two flat side faces parallel to each other, each one co-operating with a flat surface provided at the end of one leg of the U-shaped body, each pair of mutually confronting surfaces comprising the aforesaid complementary ramp and recess.

The invention will be better understood and further objects, characteristics, details and advantages thereof will appear more clearly in the course of the explanatory description which will follow with reference to the attached drawings given by way of example only and illustrating several embodiments of the invention and in which:

FIG. 2 is an exploded perspective view of a first embodiment of a fastening device according to the invention.

FIG. 3 shows an alternative embodiment of an anchoring member according to the invention.

FIGS. 4 and 5 show a member fitted with a device according to another alternative embodiment of an anchoring body according to the invention.

FIG. 6 is a perspective exploded view of a second embodiment of a fastening device according to the invention.

FIG. 7 is a perspective exploded view of a third embodiment of a fastening device according to the invention.

FIGS. 8 and 9 show two successive steps of the fastening onto a rod of an anchoring member of the embodiment according to FIG. 7.

FIGS. 10a, 10b and 10c show three successive phases of the assembly of the embodiment according to FIG. 7.

Figure 1:
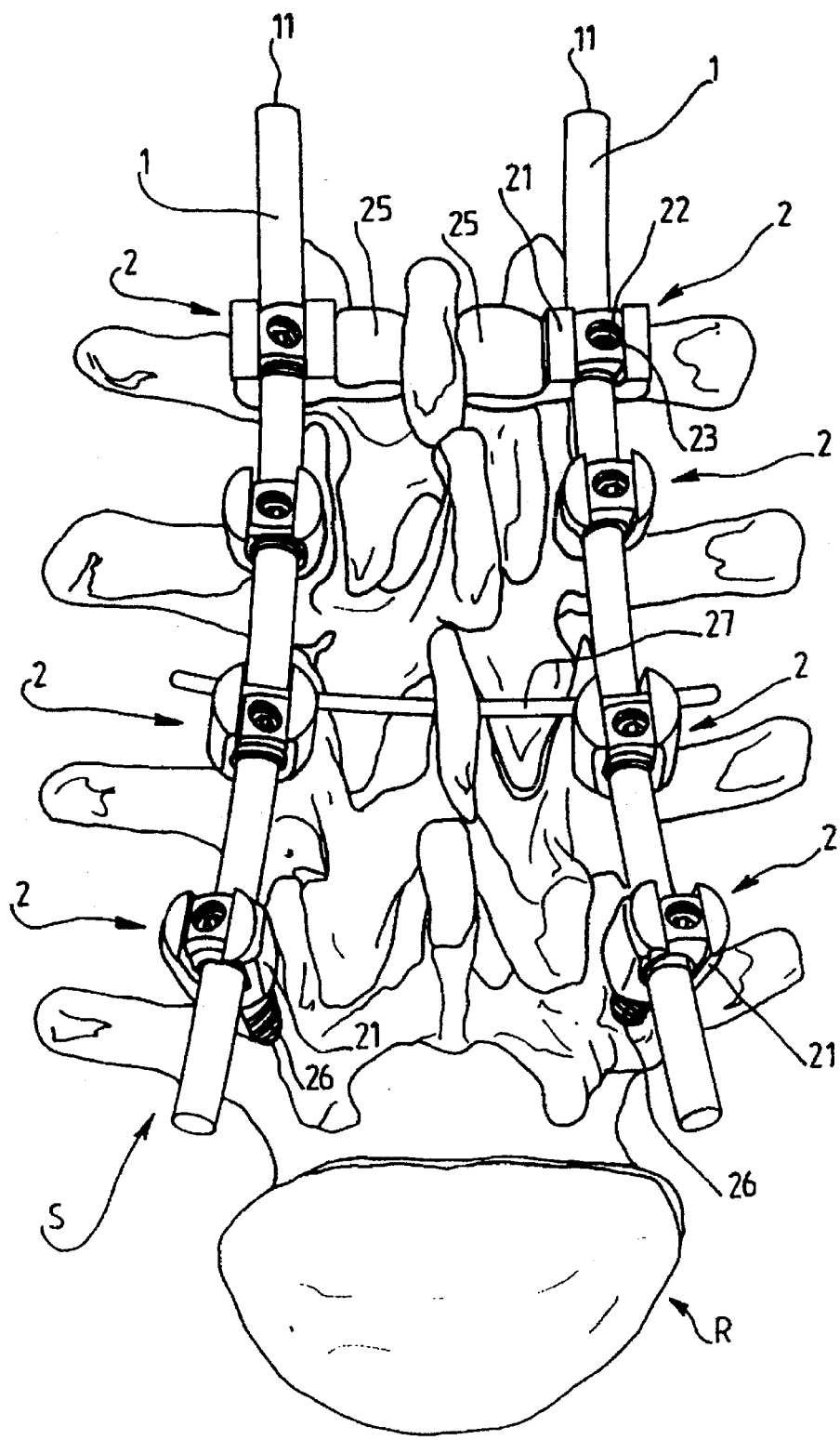
FIG. 1 is a perspective view of the rear face of a rachis section onto which a propping orthopaedic instrumentation fitted with devices according to the invention is implanted.

On FIG. 1 one sees a rachis or spinal column section R onto which is implanted an orthopaedic appliance or instrumentation S. As previously explained the appliance S comprises two staying rods 1 the longitudinal axes of which extend along the back face of the rachis R and on either side of the latter. The rods 1 are preferably made from surgical mild steel and are curved in order to exhibit a curvature selected in accordance with the rachis R to be propped.

Various members are fastened onto each rod 1 on the one hand and on the other hand are made fast to one vertebra of the rachis R or to another device fastened onto the other rod 1 of the instrumentation S.

In the first case the members will be screws, hooks or the like permitting the anchoring of the instrumentation S onto the rachis R whereas in the second one the members will act as braces connecting both rods 1.

Each one of these members is held against motion on the corresponding rod 1 with the assistance of an own fastening device.

On the figures each assembly constituted by an anchoring member or forming a brace and by its fastening device is designated in a general manner by the reference numeral 2.

Referring now to FIG. 2, one sees that the fastening device of each assembly 2 onto the rod 1 comprises a U-shaped body 21 to which the said member is made fast and between the legs of which the corresponding rod 1 may be "radially" mounted, i.e. in the direction of one of its radii and without having to be threaded therein. One should also specify here that it is the cross-section of the body 21 which is perpendicular to the longitudinal axis X—X' of the corresponding rod 1 which exhibits substantially the shape of a "U".

In addition an intermediate sleeve 22 may be mounted onto the rod 1 and caused to be accommodated through sliding between the legs of the "U" of the body 21. Clamping means 23 are provided on each sleeve 22 and made fast thereto so that they may apply a radial clamping pressure upon the rod 1.

According to the invention the rods 1 used have a circular cross-section and a smooth external surface unlike the rods used in the prior art which are either machined or provided with surface asperities.

On the other hand each one of the sleeves 22 according to the invention exhibits instead of being in the shape of a cylindrical jacket as this was the case with the known devices, substantially the shape of a slit ring or rider. One sees well on FIG. 2 that the ring 22 comprises two arcuate side wings 221 and 222 as well as a prismatic protrusion 223 projecting outwards from the ring and through which radially extends a tapped opening bore 233. It is in this bore 233 that is mounted a headless screw 23 constituting the tightening means explained hereabove.

Opposite to the bore 233 an axial slot directed along X—X' is formed in the ring 22 right through the latter. Otherwise said, the bore 233 and the axial slot of the ring 22 are disposed in front of each other along a diameter of the rod 1 onto which this ring has to be mounted. The distance between the mutually confronting axial edges of the side wings 221 and 222 which define the axial slot of the ring 22, i.e. the dimension perpendicular to X—X' of this slot is smaller than the diameter of the corresponding rod 1. However the wings are elastically deformable until the rod 1 may extend through the slot.

Concurrently the side wings of the ring 22 define an internal substantially cylindrical surface the section of which corresponds nearly to that of the rod 1. Thus since the side wings are elastically deformable, one understands that the ring 22 may be mounted onto the rod 1 radially through the said axial slot as shown by the arrow M1 on FIG. 2. In fact the wings 221 and 222 may spread apart sidewise and slide on the periphery of the rod 1 until the ring 22 comes in the position visible on FIG. 4. In this position the side wings 221 and 222 elastically clamp or hold against motion through "clipping" the rod 1 inside of the slit ring 22 while permitting their relative axial sliding.

On FIGS. 2 to 5 one sees that the side legs of the "U" of the body 21 which are designated at 211 and 212, respectively, define together a recess the shape of which corresponds substantially to that of the ring or rider 22. More especially the internal surface of the leg 211 has a generally cylindrical shape which corresponds nearly to the outer profile of the side wing 221 of the rider 22. Similarly the side wing and leg 222 and 212 exhibit corresponding respectively internal and external profiles. Thus when the ring 22 is "clipped" on or elastically engaged with the rod 1, the latter may be guided in sliding relationship along X—X' inside of the recess defined by the "U" of the body 21.

Moreover the mutually confronting ends of the side legs 211 and 212 define two flat surfaces 213 and 214, respectively, parallel to each other as well as to the axis X—X'. These flat surfaces 213 and 214 of the body 21 may co-operate with corresponding surfaces 224 and 224' of the prismatic protrusion 223 of the ring 22 in order to guide the latter along X—X' and prevent any rotation of the ring inside of the body 21.

On FIGS. 2 and 3 one remarks that the bottom of the recess defined by the "U" of the body 21 comprises a recessed portion 215 directed axially, namely along X—X'. This recessed portion 215 is diametrally opposite to the space extending between the surfaces 213 and 214 of the body and exhibit in cross-section a concave shape of an arc of a circle in the manner of a gutter. The diameter of the circle to which corresponds the arc of the gutter 215 is substantially equal to the diameter of the rod 1.

Although this has not been illustrated, the concave surface of the gutter 215 is preferably machined so as to exhibit transverse ridges (i.e. perpendicular to X—X') and/or to have a rough surface condition. This permits to increase the adherence through friction between the body 21 and the rod 1 and therefore to increase the immobilization of the latter in particular along its longitudinal direction X—X'.

One should also note here that one at least of the ends opposite along X—X' of the slit ring 22 as well as of the open body 21 comprises a chamfer. These chamfers of the ring and of the body are designated at 226 and 216, respectively. The chamfer 226 which forms a conical surface projecting axially from the ring 22 and the chamfer 216 machined in the body 21 permit to make easier the insertion of the latter into the ring 22.

On FIG. 2 the reference numeral 217 designates a shoulder projecting from the recess formed by the legs 211 and 212 and provided at that end of the "U"-shaped body which is opposite to the chamfer 216 along X—X'. This shoulder 217 constitutes an axial stop adapted to limit the sliding of the ring 22 when the latter has been previously accommodated between the legs 211 and 212 of the "U" of the body 21.

According to the embodiment of FIG. 2, the body 21 is made integral in one piece of material with an anchoring hook 24. This hook is curved along a plane parallel to the axis X—X' and projects from the body 21 opposite from the empty space between the surfaces 213 and 214. The hook 24 is provided to bear upon one of the vertebrae of the rachis R in order to participate in the anchoring of the instrumentation S thereon.

Other embodiments are illustrated on FIG. 1.

On this figure the assemblies 2 located near the upper ends 11 of the rods 1 comprise each one a curved finger 25. Like the hook 24, each finger 25 is made integral in one single piece of material with the corresponding body 21. In fact the finger 25 extends sidewise from one of the legs of the "U" of the body and is provided to anchor itself upon a vertebra of the rachis R. Otherwise said, the fingers 25 permit an anchoring and a positioning of the rods 1 in perpendicular relation to their longitudinal axes.

Near those ends of the rods 1 which are opposite to the ends 11, the assemblies 2 comprise as on FIGS. 4 and 5 anchoring screws 26 made integral in one piece of material with the corresponding body 21. Each one of these screws 26 which extends perpendicularly to X—X' and plumb with the bottom of the "U" of the body 21, is provided to accommodate itself in a bore formed in a corresponding vertebra of the rachis to be stayed R in order to constitute a stationary and firm anchoring point for the instrumentation S.

The assemblies 2 located above those which comprise the screws 26 (FIG. 1) permit to fasten between the rods 1 of the appliance S a cross-member 27 which performs the function of a brace.

Here the cross-member 27 passes inside of apertures (not shown) formed in confronting relationship in the legs of the "U" of each one of the bodies of the corresponding assemblies 2.

Since the legs 211 and 212 are like the wings 221 and 222 elastically deformable (similarly to the spacing shown at E on FIG. 5) so as to be spread apart from each other when the corresponding set screws 23 are tightened, the aforesaid apertures of each "U"-shaped body are being offset then with respect to one another. This causes the immobilization and the blocking of the cross-member 27 through buttressing of the latter in the apertures of the bodies 21. Of course as soon as the screws 23 are loosened, the corresponding apertures are aligned again and again allow a free sliding of the cross-member 27 inside of the apertures of the "U"-shaped bodies connected by the latter.

Before explaining the manner the fastening device according to the invention operates, another assembly 2 shown on FIG. 3 will now be described.

As illustrated, this assembly comprises a member constituted by an anchoring screw 28 the head of which forms a slit sleeve 281. Otherwise said, the head of the anchoring screw 28 has the shape of a cylindrical jacket threaded internally and divided into equal halves by a slot 283 parallel to the longitudinal axis of the screw. On the other hand a bore (in dotted lines) is formed in the "U" of the corresponding body 21. The screw 28 as well as one portion of the sleeve 281 are inserted into the bore of the body 21. One may also provide that that portion of the screw 28 which is inserted into the bore of the body 21 as well as the bore itself be slightly tapered in order to obtain a first positioning and a first axial blocking of the screw 28 with respect to the body 21. Once the screw 28 is in place, a suitable threaded element 282 is screwed into the threading of the sleeve 281. Under the effect of the tightening of the threaded element 282, the halves of the sleeve 281 are spreading apart and cause to press radially upon the bore of the body 21 so as to fasten the screw 28 onto the latter.

On FIG. 3 the bore of the body 21 in which is mounted the screw 28 is formed in one of the legs of the "U" of the body 21 and the axis of this screw 28 is intersecting a plane parallel to X—X' which symmetrically divides the recess defined by the legs of the "U" of the body. It however is obvious that other arrangements may be provided for the arrangement of the screw 28 as well as of the corresponding bore.

The mounting, the positioning and the immobilization of an assembly 2 fitted with the fastening device according to the invention are carried out as follows.

At first each ring 22 is mounted onto the corresponding rod 1 by displacing it according to the movement of the arrow M1 on FIG. 2 until its clipping onto this rod. Then the suitable "U"-shaped body 21 is displaced according to the movement of the arrow M2 on FIG. 2 so that the ring 22 is caused to be accommodated in the recess defined by the legs 211 and 212. In the case where the body 21 comprises a shoulder forming a stop 217, the displacement along X—X' of the body 21 is effected until the corresponding end of the ring 22 comes in contact with the stop-like shoulder 217. The rod 1 and the ring 22 may of course also be displaced for their being assembled with the body 21.

Then the assembly 2 has again a configuration such as that illustrated on FIG. 4. It is at that time only that the tightening means constituted by the screw 23 are actuated. Here the screw 23 is a headless screw with an hexagonal hollow. Under the effect of its being tightened, the screw 23 projects between the wings 221 and 222 while exerting a radial thrust onto the rod 1. As illustrated on FIG. 5, the thrust exerted by the screw 23 radially pushes the rod 1 while moving it away from the prismatic protrusion 223 so that the latter projects from the ring 22 and is caused to be applied upon the bottom of the "U" of the body 21. In the case where the body 21 has a gutter 215, it is upon this gutter that the rod 1 is caused to be pressed. This displacement of the rod 1 causes a simultaneous and opposite displacement of the ring 22 inside of the body 21. Otherwise said under the effect of the tightening of the means 23, the ring 22 is moved radially away from the bottom of the body 21. During this displacement the wings 221 and 222 slide on the periphery of the rod and are spreading apart until the edge of each one of their free ends is caused to clamp a generatrix of the rod 1.

One remarks here that the contact between the body 21 and the rod 1 is at least linear and at the surface in the case where the body has a gutter 215 whereas the contact between the slit sleeve 22 and this rod 1 is effected along two diagonally opposite generating lines of the latter. Therefore in comparison with the prior art the zones of contact with the rod 1 through the medium of which its immobilization is carried out are considerably greater.

In order that the edges of the free ends of the wings 221 and 222 exert upon the rod 1 a clamping directed towards the axis X—X' under the effect of the tightening of the screw 23, the external upper portion of each one of its wings, namely the external surfaces closest to the prismatic protrusion 223 co-operates with and is made fast to one of the corresponding surfaces of the legs 211 and 212. The action upon these surfaces also causes the fastening through a wedging effect of the ring 22 within the body 21.

For that purpose these surfaces are located plumb with the wings 221 and 222 and converge towards each other. On FIG. 1 these surfaces of the body 21 and of the ring 22 have a profile shaped as an arc of a circle but one also may provide that they be flat and converge outwards as well as towards the plane of symmetry of the ring 22.

It should be noted here that the wedging effect obtained according to the invention and owing to which the body 21 and the ring 22 are assembled makes use of forces and pressures directed in the radial direction of the rod 1. This is completely different from some devices of the prior art in which a body and a sleeve are assembled while causing a wedging effect with the assistance of frusto-conical surfaces the generating lines of which converge towards the axis of the rod and therefore are inserting into each other in the axial direction of the latter.

One should also emphasize that the legs 211 and 212 are spreading apart slightly under the tightening effect of the screw 23 as shown at E on FIG. 5.

Moreover in all the known devices once the intermediate sleeve has been mounted on the rod, the latter is constantly maintained and held against motion on this rod. On the contrary with the present invention after the clipping of the ring 22 onto the rod 1, the tightening means cause a radial displacement of this ring. It is this displacement which permits to obtain the assembly of the body 21 and of the ring 22.

Another considerable advantage of the present invention consists in that even if the tightening means 23 are loosened the assembly 2 remains immovable on the rod 1. Furthermore the device according to the invention differentiates also from the prior art in that the forces applied by the tightening screw 23, the wings 221 and 222 as well as the bottom of the body 21 generate in that rod 1 forces converging towards the axis X—X' of the rod and directed like a cross when the device is viewed transversely as on FIG. 5.

FIG. 6 shows a second embodiment of the invention which distinguishes from the first one shown on FIG. 2 by the fact that the sleeve 22 is provided in the shape of a substantially cylindrical slit ring which comprises as being diametrally opposite to the bore 223 of the prismatic protrusion 23, an axial slot with a relatively small width. Thus the side wings 221, 222 of the ring 22 define a substantially cylindrical internal surface the section of which corresponds nearly to that of the rod 1. The ring 22 may be slipped axially over the smooth rod 1 as this is shown by the arrow M3 on FIG. 6. In that position the side wings 221 and 222 are tightly enclosing the rod 1 inside of the slit ring 22 while permitting their relative axial sliding.

In this embodiment the rod under the effect of the tightening means is spreading apart the free ends of the wings 221, 222 of the ring 22 to ensure their radial pressing upon the legs 211, 212 of the body 21 which thus retain the ring within this body by a wedging effect but which keeps bearing upon these ends so as to be held immovable within the ring by clamping along two generating lines. FIGS. 8 and 9 illustrate this immobilization effect of the rod within the ring in the "U"-shaped body.

FIG. 7 shows an advantageous embodiment of the invention. In this case too the sleeve 22 is provided in the shape of a slit ring which exhibits a slot with a relatively small width according to the embodiment of FIG. 6, so that the legs 221, 222 define a substantially cylindrical recess for the rod 1. As in the case of FIG. 6, the ring is mounted on the rod through axial slipping symbolized by the arrow M3. One further sees that the side legs 211, 212 of the "U"-shaped body 21 define a substantially cylindrical housing the shape of which corresponds to that of the ring 22.

An essential peculiarity of this embodiment resides in the fact that each flat face 224, 224' of the prismatic protrusion 223 of the ring 22 exhibits in its axially central portion a set-off 231 in the shape of a cylindrical segment. In a complementary fashion each one of the flat faces 213, 214 of the ends of the side legs 211, 212 of the body 21 exhibits a recess 218 in the shape of an arc of a circle into which the set-off 231 of the ring 22 will extend when the latter is lying in its assembling position of the fastening device according to the invention. In this manner the ring is axially locked in both directions.

One further sees that the ring 22 comprises at the root of each flat side face 224, 224' of the prismatic protrusion 223 a flat shoulder face 227, 227'. Each face extends in substantially perpendicular relation to the axis of the tightening means or is slightly inclined with respect to this axis towards the axis of the ring. In a complementary fashion each end of one wing 211 or 212 of the body 21 comprises in its internal portion a flat face 215, 215' forming a bearing face of a face 227, 227' of the ring as shown by the FIGS. 8 and 9. One thus obtains a perfect jamming of the sleeve 22 within the body 21 owing to the shapes and pressures directed radially with respect to the rod. FIGS. 8 and 9 also show that owing to the co-operation of the surfaces 227 and 227' of the ring and of the surfaces 217 and 217' of the body, one avoids a spreading apart of the free ends of the legs of the body and any accidental disengagement of the ring from the body 21.

One should further note that at least one of the ends opposite along the axis X—X' of the slit ring 22 as well as of the body 21 comprises a chamfer. These chamfers of the ring and of the body are designated at 226 and 216, respectively. The chamfer 226 which forms a conical surface axially projecting from the ring 22 and the chamfer 216 machined in the body 21 permit to make easier the insertion into the latter of the ring 22.

FIGS. 10a to 10c illustrate the mounting, the positioning and the immobilization of the assembly fitted with the fastening device according to the embodiment of FIG. 7. At first each ring 22 is mounted onto the corresponding rod 1 by displacing it according to the arrow M3 of FIG. 7. Then the suitable body 21 is displaced according to the arrow M4 of FIG. 7 so that the ring 22 is caused to be accommodated in the recess defined by the legs 211 and 212 until the set-off portions 231 of the ring 22 be in contact with the edges of the faces 213, 214 of the body 21. The ring 22 is then inserted through forced sliding causing the spreading apart of the faces 213 and 214 in an elastic manner until the cylindrical convex surfaces of the set-off portions 231 are placing themselves into their complementary concave cylindrical recessed portions 218 of the body 21. The faces 213 and 214 of the body then assume their initial position again.

The invention is of course not at all limited to the embodiments which have just been illustrated and comprise all the equivalents as well as the combinations of the means described if the latter are carried out according to its gist.

We claim:

1. An arrangement for fastening a member on a rod for a rachidian orthopaedic instrumentation, comprising:

a U-shaped body adapted to be secured to said member, said U-shaped body having a bottom portion and two legs extending from said bottom portion, said legs having inner faces facing toward one another and free ends, and wherein the rod is insertable between said legs;

an intermediate sleeve having substantially the shape of a slit ring adapted to be mounted onto the rod and within said U-shaped body, said intermediate sleeve having wings, each of said wings defining a free end and wherein said free ends of said wings define a slot therebetween, said wings further having opposing inner faces and outer faces substantially opposite from said inner faces, clamping means secured to said intermediate sleeve and adapted to exert a radial pressure upon the rod situated in said intermediate sleeve such that the rod is pushed in a direction towards said slot, and wherein said slot of said intermediate sleeve has a width, said width being smaller than the diameter of the rod such that the rod is adapted to move toward said slot upon said exertion of said radial pressure upon the rod by said damping means such that the rod bears against said free ends of said wings and axial motion of the rod in relation to said intermediate sleeve is prevented and the rod causes said wings to spread apart thereby enlarging said slot such that said outer faces of said wings are pressed against said inner face of said legs of said U-shaped body to securely retain said intermediate sleeve within said U-shaped body by a wedging effect.

2. A device according to claim 1, wherein the intermediate sleeve is engaged radially through elastic clamping with the rod and in that under the effect of the radial pressure exerted by said clamping means, the rod projects from the ring while being applied upon the bottom portion of the "U" of the body for producing the wedging effect and for preventing said axial motion of said rod.

3. A device according to claim 1, wherein the bottom portion of the "U" of the body comprises an axial recess in the shape of a gutter and corresponding to the diameter of the rod.

4. A device according to claim 3, wherein said gutter exhibits a rough surface condition in order to increase the adherence through friction between the rod and the body.

5. A device according to claim 1, wherein the member is an anchoring screw having a head formed by a sleeve portion provided with an axially extending slit and an inner thread, and said U-shaped body is provided with a bore wherein the screw is inserted, and a threaded element is engaged in the sleeve portion to cooperate with the inner thread of the sleeve portion and is adapted to enlarge the diameter of the sleeve portion when thread therein.

6. A device according to claim 5, wherein the bore is formed in one leg of the U-shaped body.

7. A device according to claims 1, wherein at least one of the opposing ends of the slit ring and U-shaped body are chamfered.

8. A device according to claim 1, wherein the intermediate sleeve is engageable with the rod through axial slipping over, the slot having a width smaller than the rod so that in the spread apart condition under the effect of the clamping means, the rod keeps bearing upon the inner faces of the wings which define the slot.

9. A device according to claim 1, wherein the intermediate sleeve comprises an outer radial prismatic protrusion situated diametrally opposite to the slot and which comprises at least one lateral surface parallel to the axis of the ring, and the U-shaped body comprises at the end of at least one of the legs a flat face parallel to the lateral face of the ring adapted to come in contact with the lateral face when the ring mounted in the U-shaped body and the at least one lateral face and of the flat face of the U-shaped body comprises a protruding portion and the other face comprises a recess of complementary shape so that the ring is axially locked in the U-shaped body through engagement of the protruding portion in the recess.

10. A device according to claim 9, wherein the prismatic protrusion comprises two lateral flat faces parallel to each other, each one co-operating with the flat surface provided at the end of one leg of the U-shaped body, each pair of mutually confronting surfaces formed of one lateral flat face of a prismatic protrusion and a flat face of a leg comprising a protruding portion and recess of complementary shape.

11. A device according to claim 9, wherein the protruding portion exhibits the shape of a cylindrical segment.

12. A device according to claim 10, wherein the prismatic protrusion comprises at the base of said at least one lateral face, a face which is substantially perpendicular with respect to a diametral middle axial plane passing through the middle of the slot of the ring and in that the body comprises at the end of each leg a face adapted to constitute a bearing face of the faces of the ring.

13. An arrangement according to claim 1, wherein said free ends of said wings are defined by curved portions.

14. An arrangement according to claim 1, wherein said free ends of said wings face toward one another.

15. An arrangement for fastening a member on a rod for a rachidian orthopaedic instrumentation, comprising:

a U-shaped body adapted to be secured to said member, said U-shaped body having a bottom portion and two legs extending from said bottom portion, said legs having inner faces facing toward one another and free ends, and wherein the rod is insertable between said legs;

an intermediate sleeve having substantially the shape of a slit ring adapted to be mounted onto the rod and within said U-shaped body, said intermediate sleeve having wings, each of said wings defining a free end and wherein said free ends of said wings define a slot therebetween, said wings further having opposing inner faces and outer faces substantially opposite from said inner faces, clamping means secured to said intermediate sleeve and adapted to exert a radial pressure upon the rod situated in said intermediate sleeve such that the rod is pushed in a direction towards said slot, and wherein the member is an anchoring screw having a head formed by a sleeve portion provided with an axially extending slit and an inner thread, and said U-shaped body is provided with a bore wherein the screw is inserted, and a threaded element is engaged in the sleeve portion to cooperate with the inner thread of the sleeve portion and is adapted to enlarge the diameter of the sleeve portion when thread therein.

* * * * *